(12) United States Patent
Cyphery et al.

(10) Patent No.: US 8,752,427 B2
(45) Date of Patent: Jun. 17, 2014

(54) FUNCTIONAL CAPACITY EVALUATOR

(75) Inventors: Charles D. Cyphery, Albuquerque (MX); Marco N. Vitiello, Miami, FL (US)

(73) Assignee: Med-Tek LLC, Coconut Grove, FL (US)

( * ) Notice: Subject to any disclaimer, the term of this patent is extended or adjusted under 35 U.S.C. 154(b) by 101 days.

(21) Appl. No.: 13/289,614

(22) Filed: Nov. 4, 2011

(65) Prior Publication Data

US 2012/0137771 A1 Jun. 7, 2012

Related U.S. Application Data

(60) Provisional application No. 61/344,893, filed on Nov. 5, 2010.

(51) Int. Cl.
*A61B 1/24* (2006.01)
(52) U.S. Cl.
USPC .......................................................... 73/379.02
(58) Field of Classification Search
USPC .............................. 73/379.02, 379.01, 379.03
See application file for complete search history.

(56) References Cited

U.S. PATENT DOCUMENTS

| | | | |
|---|---|---|---|
| 4,607,841 A * | 8/1986 | Gala | 482/91 |
| 5,125,270 A | 6/1992 | Kovacevic | |
| 5,170,663 A | 12/1992 | Kovacevic | |
| 5,254,066 A * | 10/1993 | Brown et al. | 482/137 |
| 5,269,738 A | 12/1993 | Boren | |
| D579,563 S | 10/2008 | Hensler et al. | |
| D580,549 S | 11/2008 | Schwartz et al. | |
| D653,338 S | 1/2012 | Mangeshikar | |
| 2003/0125171 A1 | 7/2003 | He | |
| 2004/0220490 A1 | 11/2004 | Appel et al. | |
| 2005/0021294 A1 | 1/2005 | Trsar et al. | |
| 2007/0074720 A1 | 4/2007 | Schwartz et al. | |
| 2007/0167859 A1 | 7/2007 | Finneran et al. | |
| 2009/0299210 A1 | 12/2009 | Marcarian | |
| 2009/0326406 A1 | 12/2009 | Tan et al. | |
| 2012/0137771 A1 | 6/2012 | Cyphery et al. | |
| 2012/0143064 A1 | 6/2012 | Cyphery et al. | |

OTHER PUBLICATIONS

United States Notice of Allowance issued in U.S. Appl. No. 29/405,718 mailed on Apr. 24, 2013.
Notice of Allowance issued in Design U.S. Appl. No. 29/405,718 dated Apr. 24, 2013.
International Search Report issued in International Patent Application No. PCT/US11/59393 dated May 9, 2012.

\* cited by examiner

*Primary Examiner* — Jewel V Thompson
(74) *Attorney, Agent, or Firm* — McDermott Will & Emery LLP

(57) ABSTRACT

A functional capacity evaluator has a strain block and a strain gauge attached to the strain block. A first pair of grips is attachable to the strain block such that when a user squeezes them together using a grip motion, the strain block and strain gauge are flexed for measuring the user's grip strength. A second pair of grips is attachable to the strain block such that when the user squeezes them together using a pinch motion, the strain block and strain gauge are flexed for measuring pinch strength. A deadlift bar is attachable to the strain block such that when the strain block is supported in a first direction and the user pulls on the bar in an opposing direction, the strain block and strain gauge are flexed for measuring deadlift strength.

14 Claims, 7 Drawing Sheets

US 8,752,427 B2

FUNCTIONAL CAPACITY EVALUATOR

RELATED APPLICATION

This application claims priority of U.S. provisional application No. 61/344,893 filed on Nov. 5, 2010, the entire contents of which are incorporated by reference herein.

TECHNICAL FIELD

The present disclosure relates to a functional capacity evaluator (FCE) for measuring grip strength, pinch strength, and deadlift strength, usable in a system to evaluate muscle functions and strength of a patient.

In dynamic muscle function monitoring and evaluating systems, sensors are attached to various parts of a patient's body for data collection. The details of such a system are described in a co-pending application filed on Nov. 4, 2011, concurrently with this application, the entire contents of which are incorporated by reference herein. In this system, sensor data is directly fed into a point of detection (POD) device for conditioning, acquiring, and transmitting the sensor data. The sensors include, for example, but are not limited to, a surface EMG (sEMG) sensor, a motion detection sensor, and an FCE such as a conventional FCE or the FCE disclosed herein. The POD device acquires continuous analog signals, conditions them, and then digitizes these signals These digital data are then transferred wirelessly to a computer system for processing using software.

The system can monitor and record the data measured by the sEMG sensors attached to various muscle groups in the human body. While acquiring the sEMG signals, the system can simultaneously acquire a motion sensor signal responsive to the body motion and/or a signal responsive to muscle strength from the FCE. The system can be specialized to test, for example, cervical, thoracic and lumbar spines as well as upper and lower extremities. The system can collect and display muscle function data and characteristics including tone, fatigue, as well as other activities that take place in the muscle. This system can be used in a number of arenas such as occupational and sports medicine, and rehabilitation clinics.

Conventional FCEs use three separate off-the-shelf sensors, one for each test (grip strength, pinch strength, and deadlift strength), that are very expensive and aesthetically displeasing. The present disclosure provides a reduced-cost FCE combining all sensors into a single unit, which is also more convenient to use and can be styled for improved aesthetics.

SUMMARY

The present disclosure provides a functional capacity evaluation device that performs three different functions. The device comprises a grip measurement portion for measuring a strength of a grip motion; a pinch measurement portion for measuring a strength of a pinch motion; a deadlift measurement portion for measuring a strength of a deadlift motion; and a strain gauge for obtaining values of the strength of the grip motion, pinch motion and deadlift motion.

In the aforementioned device, a functional capacity evaluator comprises a strain block, and a strain gauge attached to the strain block. A first pair of grips is attachable to the strain block such that when a user squeezes the first pair of grips together using a grip motion, the strain block and strain gauge are flexed for measuring a grip strength of the user. A second pair of grips is attachable to the strain block such that when the user squeezes the second pair of grips together using a pinch motion, the strain block and strain gauge are flexed for measuring a pinch strength of the user. A deadlift bar is attachable to the strain block such that when the strain block is supported in a first direction and the user pulls on the deadlift bar in a second direction opposite the first direction using a deadlift motion, the strain block and strain gauge are flexed for measuring a deadlift strength of the user.

In the aforementioned device, the first pair of grips includes a first lever fixed to the strain block, and a second lever movably attached to the strain block.

In the aforementioned device, the second lever is adjustably attached to the strain block to accommodate the size of a hand of the user.

In the aforementioned device, the second lever is slidably attached to the strain block.

In the aforementioned device, the strain block includes a plunger for adjusting a position of the second lever on the strain block, the second lever includes plural holes, and each of the plural holes is configured to receive the plunger.

In the aforementioned device, the strain block includes plural holes, the second lever includes a plunger for adjusting a position of the second lever on the strain block, and each of the plural holes is configured to receive the plunger.

In the aforementioned device, the second pair of grips includes a first pinch lever and a second pinch lever, and the first and second pinch levers are disposed at respective ends of the first and second levers of the first pair of grips.

In the aforementioned device, the deadlift measurement portion includes a bar with two grips.

In the aforementioned device, the deadlift bar includes a clamp portion for attaching the bar to the strain block.

In the aforementioned device, the bar and the clamp portion is detachable from the strain block.

In the aforementioned device, the strain block includes an attachment portion for attaching an anchoring member to the strain block for supporting the strain block in the first direction.

In the aforementioned device, the strain gauge is a single strain gauge.

In the aforementioned device, the anchoring member is a strap, and the attachment portion comprises a clevis for attaching the strap to the strain block.

In another embodiment of the aforementioned device, the first pair of grips includes a first lever and a second lever, a and the second pair of grips includes a first pinch lever and a second pinch lever. The first lever comprises the strain block, and the first pinch lever is disposed at a first end of the first lever. The second lever is attached to the strain block remote from the first end of the first lever and extends toward the first end of the first lever, and the second pinch lever is disposed at an end of the second lever proximal the first end of the first lever. The second lever comprises an adjustable grip portion to accommodate the size of a hand of the user.

DETAILED DESCRIPTION

Figure 1:
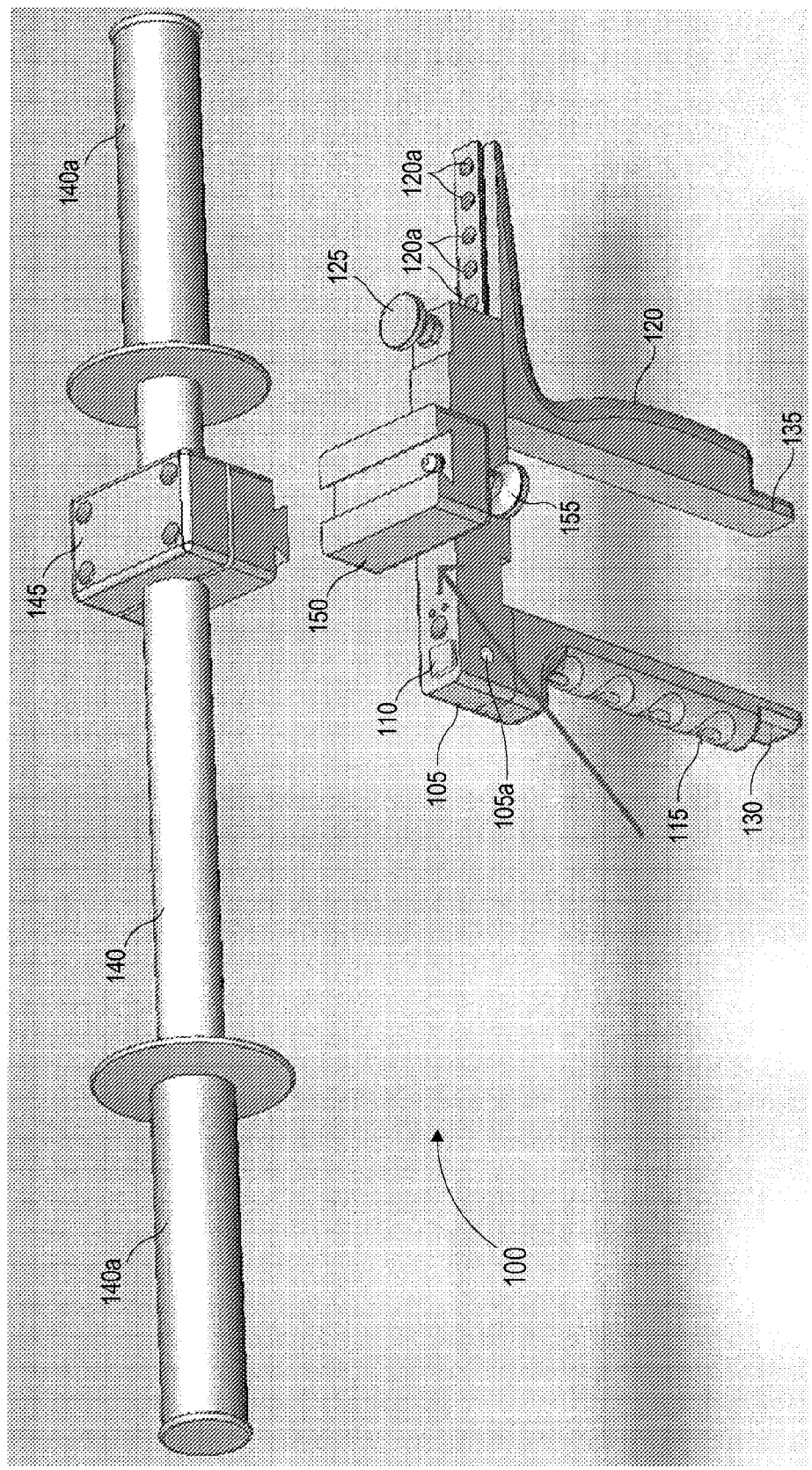
FIG. 1 shows an exemplary perspective view of a functional capacity evaluator of an embodiment of the present disclosure.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, components, and/or materials have been described at a relatively high-level, without detail, in order to avoid unnecessarily obscuring aspects of the present teachings.

The disclosed FCE has a single strain gauge attached to a top structural member. The positioning of the strain gauge enables the top structural member to be used as the flexing member for all three exercises (i.e., grip, pinch, and deadlift). For measuring grip strength and pinch strength, the deadlift bar need not be attached.

An embodiment of the disclosed FCE will now be described with reference to FIGS. 1-6. FCE 100 includes a strain block 105 to which is attached, as by epoxy or other suitable adhesive, a single strain gauge 110. Strain gauge 110 is a conventional strain gauge, such as Model SGT-2/1000-FB13 available from Omega Engineering, Inc. of Stamford, Conn. Strain gauge 110 includes a wiring harness (not shown) for attachment to a power source and a signal processing device in a conventional manner. A first pair of grips 115, 120 is attachable to the strain block 105 such that when a user squeezes the first pair of grips 115, 120 together using a grip motion, the strain block 105 and strain gauge 110 are flexed for measuring a grip strength of the user.

The first pair of grips comprises first lever 115 fixed to the strain block 105 via, for example, threaded fastener(s), and second lever 120 movably attached to the strain block 105. The second lever 120 is adjustably attached to the strain block 105; for example, slidably attached to strain block 105, to accommodate the size of a hand of the user. In the embodiment shown in the figures, the strain block 105 includes a spring-loaded plunger 125 for adjusting a position of the second lever 120 on the strain block 105, and the second lever 120 includes plural holes 120a, each of which is configured to receive the plunger 125. It will be understood by those skilled in the art that, in other embodiments, the strain block 105 could instead include plural holes, and the second lever 120 could include a plunger for adjusting a position of the second lever 120 on the strain block 105, each of the plural holes being configured to receive the plunger.

Figure 2:
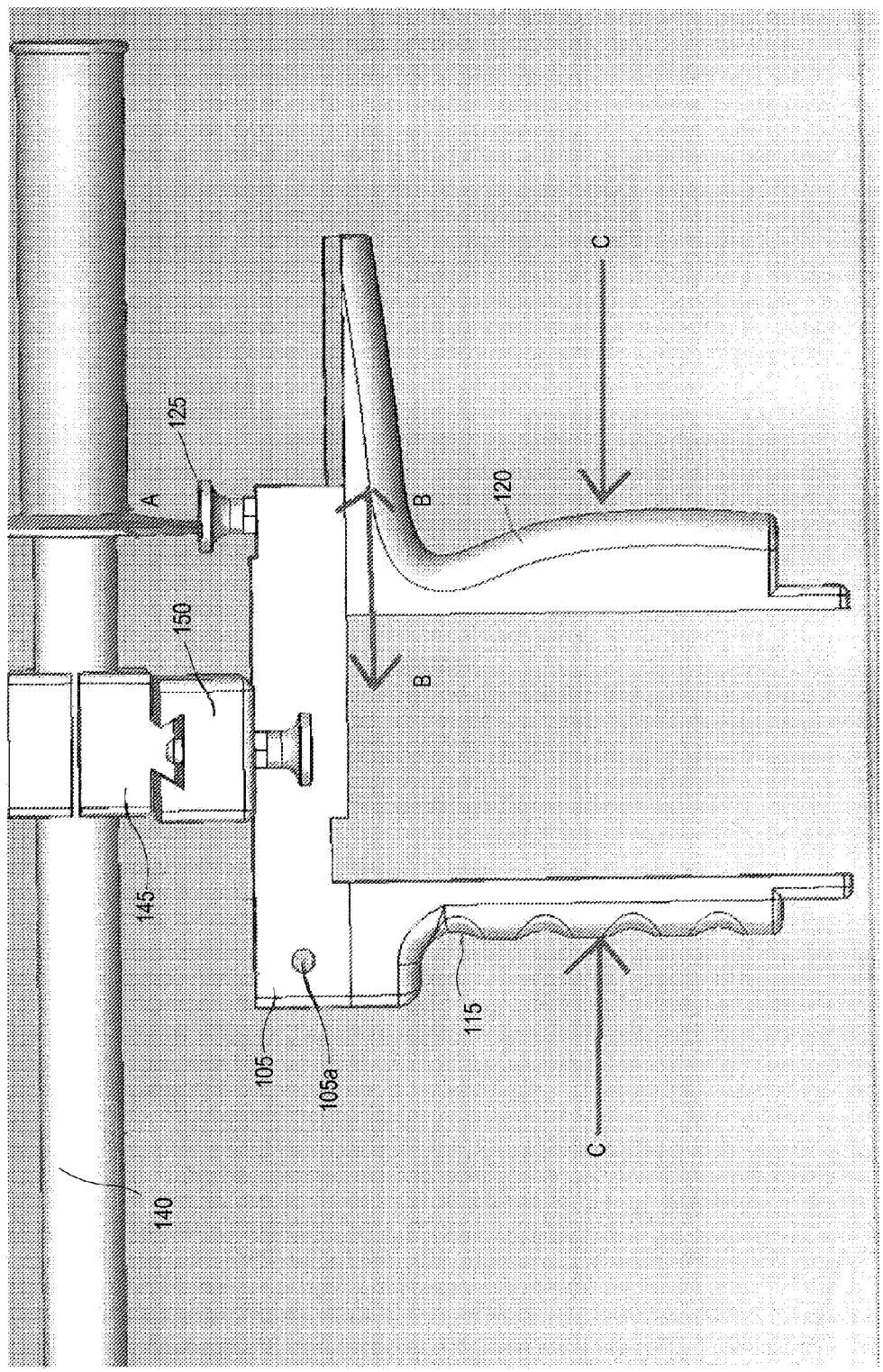
FIGS. 2 and 3 show a side view of the functional capacity evaluator of FIG. 1.

Referring now to FIG. 2, the top arrow A shows the direction of motion for the plunger 125 which when pulled up allows the second lever 120 to slide back and forth as shown by arrows B, adjusting the size of the grip to a number of different positions according to holes 120a. When the user squeezes the levers 115, 120 in the directions of arrows C, the strain block 105 and strain gauge 110 flex, resulting in a relative force value reading (calculated from calibrated gauge factors in a well-known manner) corresponding to the force applied.

A second pair of grips 130, 135 is attachable to the strain block 105 such that when the user squeezes the second pair of grips together using a pinch motion, the strain block 105 and strain gauge 110 are flexed for measuring a pinch strength of the user. The second pair of grips includes a first pinch lever 130 and a second pinch lever 135, which are disposed at respective end of the first and second levers 115, 120.

Figure 3:
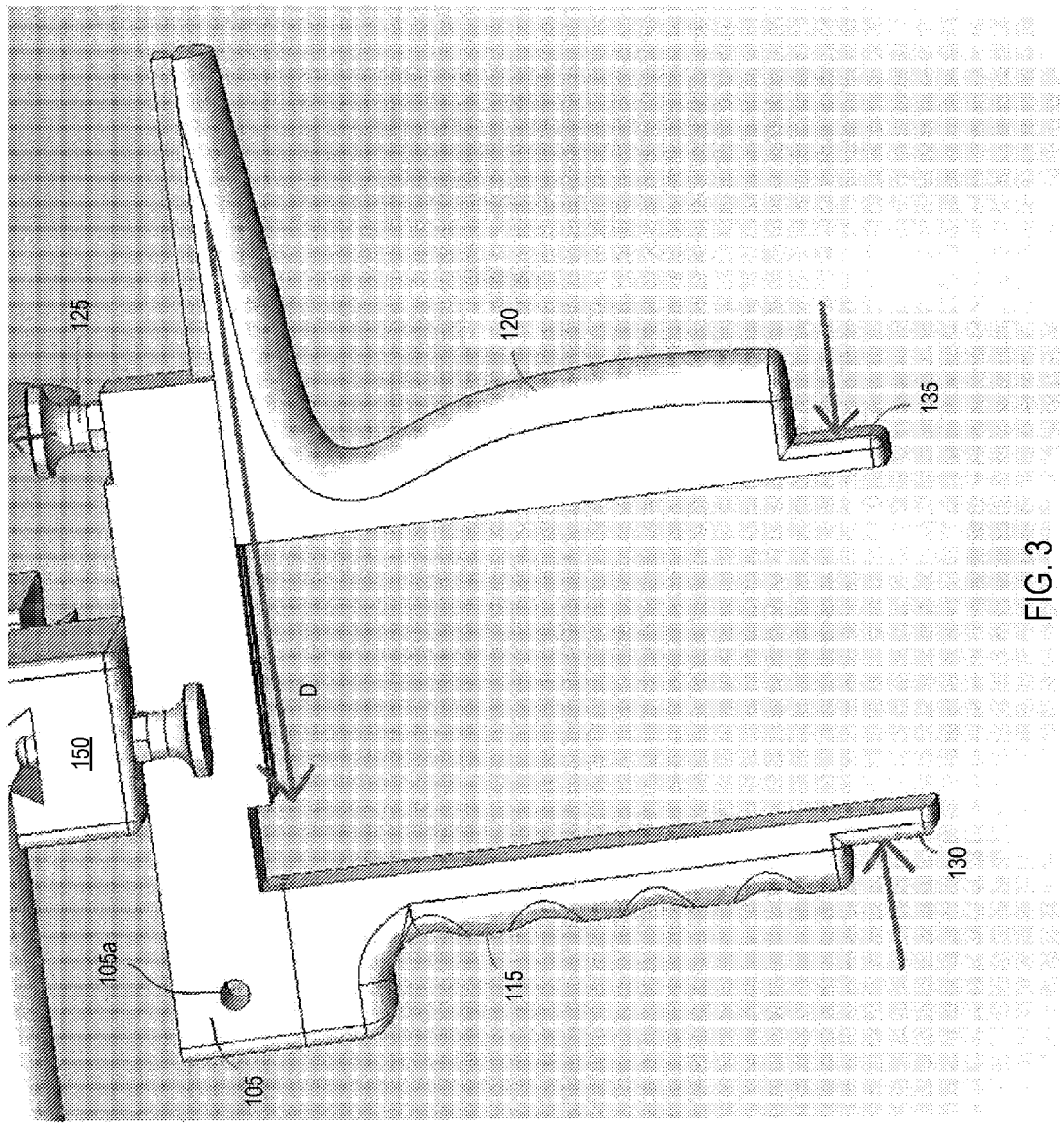
Figure 4:
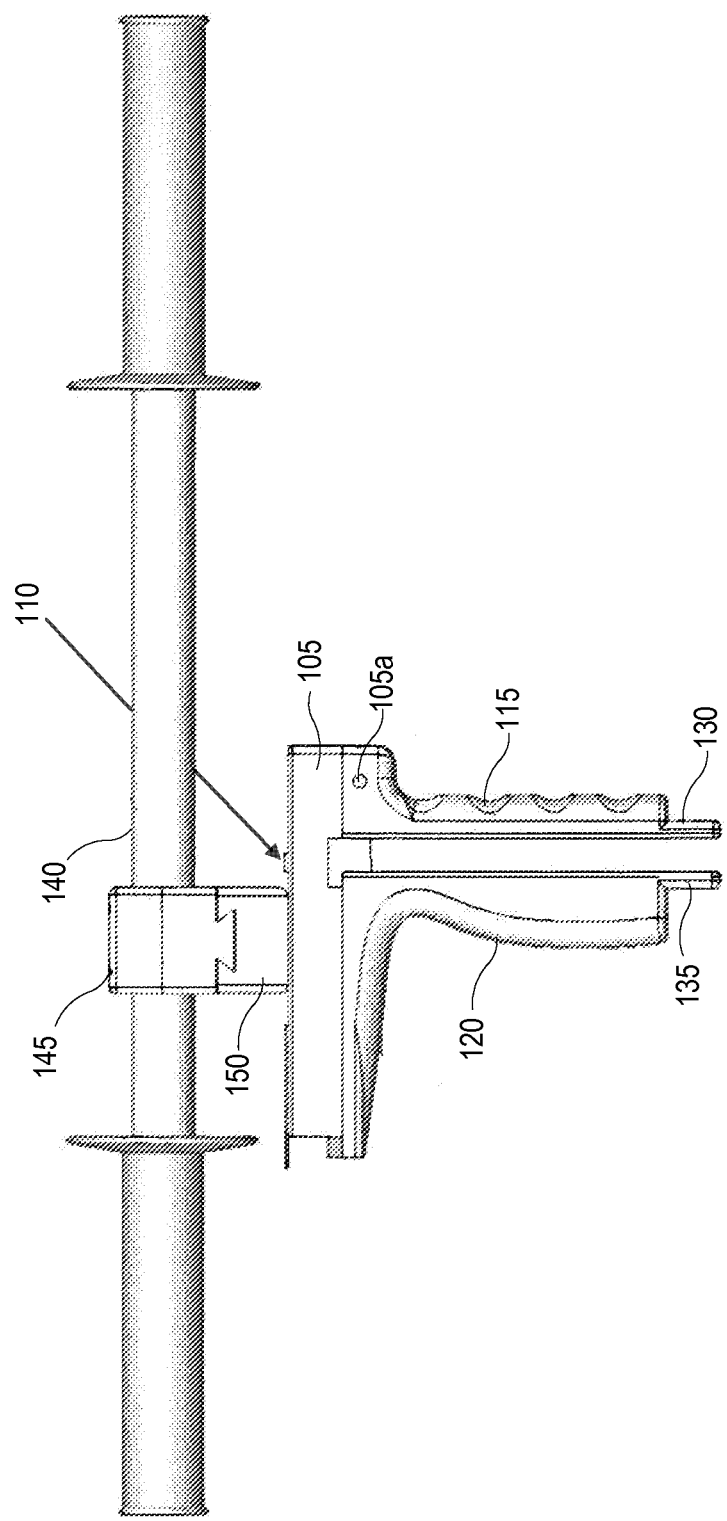
FIG. 4 shows another side view of the functional capacity evaluator of FIG. 1.
Figure 5:
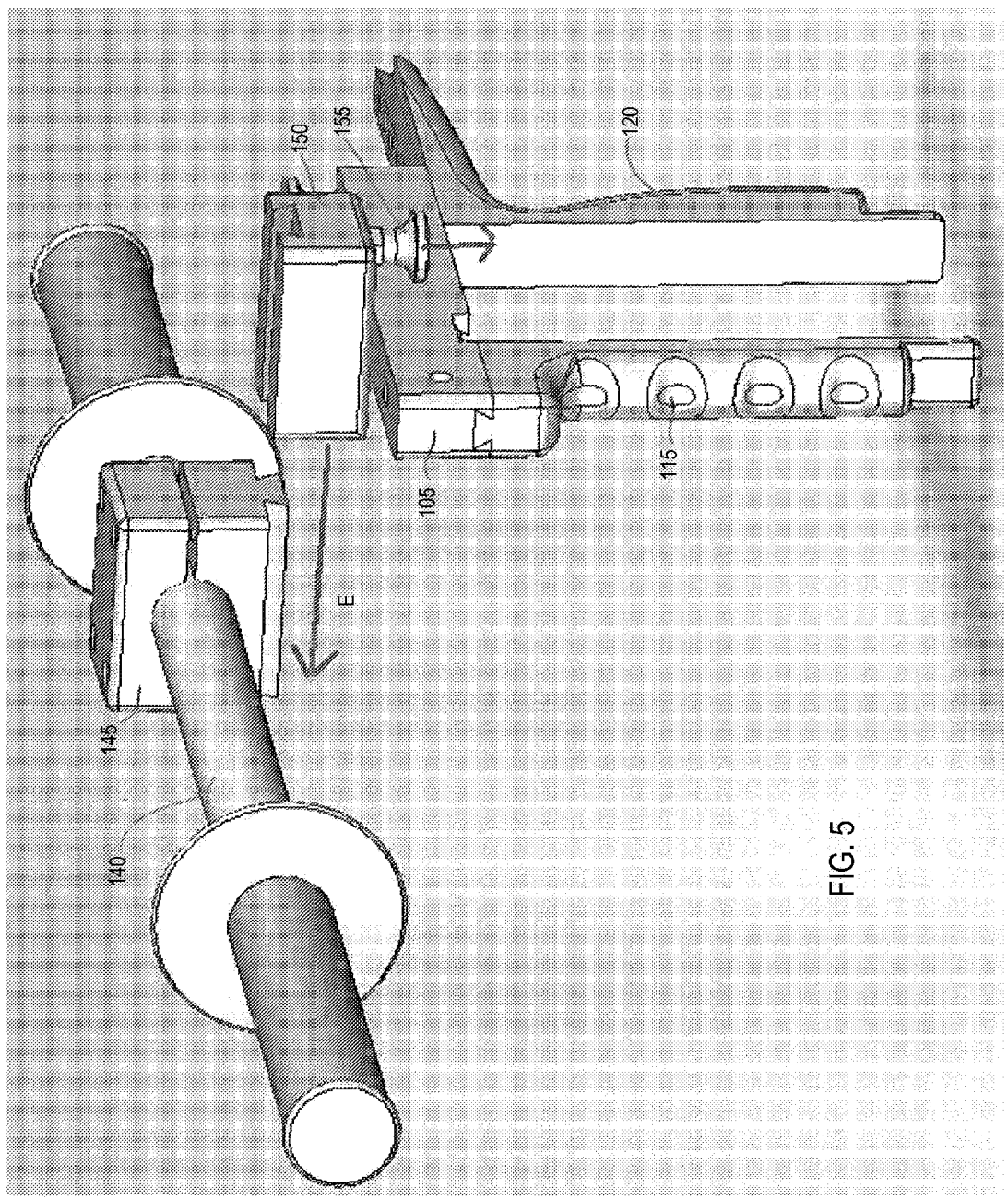
FIG. 5 shows another perspective view of the functional capacity evaluator of FIG. 1.
Figure 6:
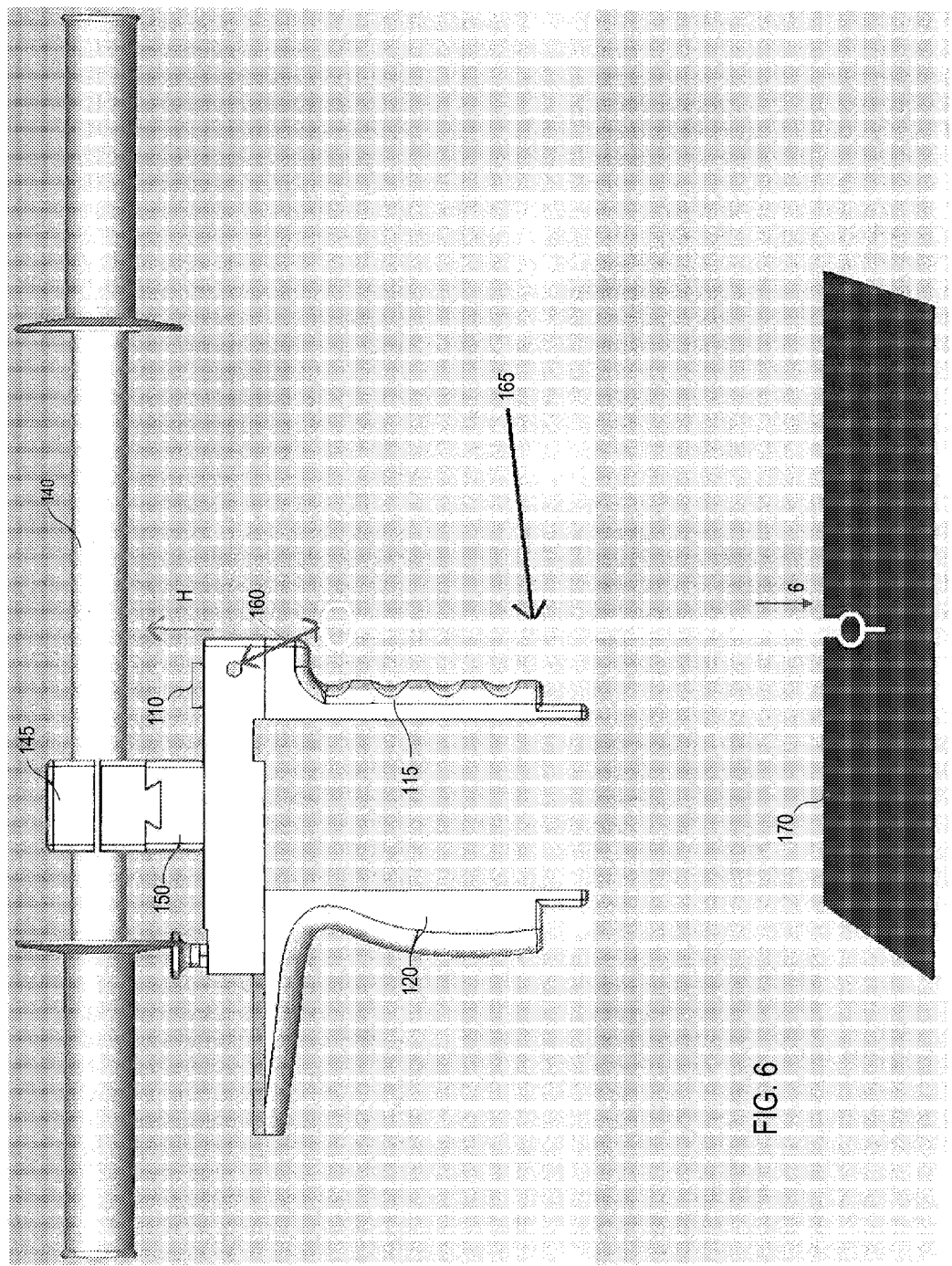
FIG. 6 shows a side view of the functional capacity evaluator of FIG. 1 with a strap attached.

For conducting the pinch exercise, as shown in FIGS. 3 and 4, the sliding second lever 120 is moved as close to the first lever 115 as possible (in the directly of arrow D) using the plunger 125, thereby placing the two pinch levers 130, 135 at their closest location to each other, which mimics the size of a conventional pinch device. Because of the longer lever action of the first lever 115, the force seen in the strain block 105 will not be considerably lower than that seen during the grip test, despite the pinch being of significantly lower force than the grip.

A deadlift bar 140 is attachable to the strain block 105 such that when the strain block 105 is supported in a first direction and the user pulls on the deadlift bar 140 in a second direction opposite the first direction using a deadlift motion, the strain block 105 and strain gauge 110 are flexed for measuring a deadlift strength of the user. The deadlift bar 140 has two grips 140a at its ends, and a clamp portion 145 for attaching and detaching the bar 140 to the strain block 105. Strain block 105 has a corresponding clamp portion 150 for engaging with clamp portion 145 of bar 140, as by sliding. Clamp portion 145 has a hole (not shown) for engaging a spring-loaded plunger 155 for positively retaining bar 140 on strain block 105.

For conducting the deadlift exercise, the bar 140 and the strain block 105 are mated together by sliding in the direction of arrow E while plunger 155 is pulled in the direction of arrow F (see FIG. 5) allowing the components to slide and lock together. The strain block 105 includes a through-hole 105a for attaching an attachment portion, such as a clevis 160, to the strain block 105 (see FIG. 6). Clevis 160 attaches one end of an anchoring member, such as an adjustable strap 165, to the strain block 105 for supporting the strain block in the first direction, shown by arrow G. A plate 170 on the floor is attached to the other end of the strap 165.

The hole 105a is positioned approximately in the middle of the bar 140 to ensure a balanced force when the bar 140 is pulled in the second direction (i.e., the direction of arrow H). The user steps on the plate 170 with the strap 165 adjusted to an appropriate height as dictated by the test protocol, and the bar 140 is pulled up in the direction of arrow H, flexing the strain block 105 and strain gauge 110. The strain gauge 110 measures the force. Hole 105a is located in the strain block 105 so that this lever action is much shorter to accommodate the greater force of the deadlift exercise.

The FCE 100 utilizes a single full bridge strain gauge mounted to allow accurate readings from all three exercises without sacrificing resolution between measurements of differing force levels. The grip test allows adjustments to grip span with a finer resolution and wider and smaller span than a conventional device (e.g., a Jamar Grip). The pinch test allows measurements to be made in a fashion similar to a conventional load cell and can also be adjusted to different pinch spans. The isometric function test (deadlift test) measures asymmetric performance against an immovable footplate; e.g. plate 170.

The disclosed FCE utilizes strain gauge 110 configured in a Wheatstone bridge arrangement to which is supplied an excitation voltage (e.g., +/−5 VDC). The bridge returns a proportional voltage relative to the strain seen at the strain block 105. This voltage value is fed into simple signal conditioning circuitry in a conventional manner, to bring the voltage levels up to a level that matches the input voltages of the downstream analog to digital converters (ADCs).

Figure 7:
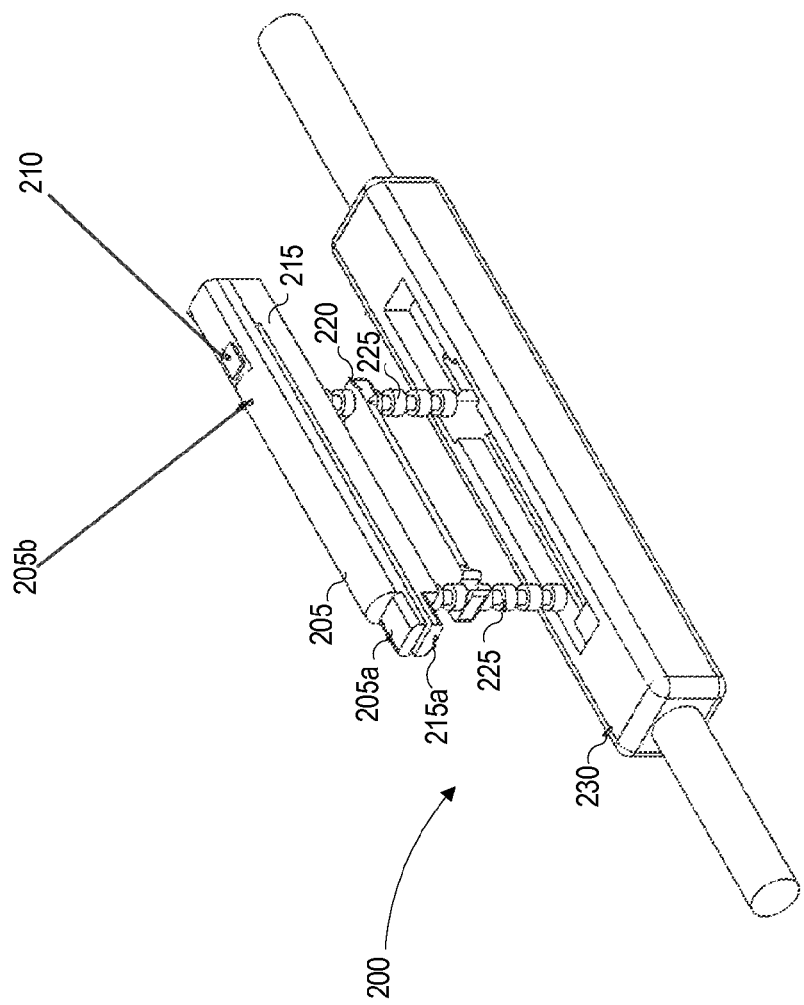
FIG. 7 shows a perspective view of a functional capacity evaluator of a further embodiment of the present disclosure.

An alternative embodiment of the disclosed FCE is shown in FIG. 7. FCE 200 operates on the same principles as the embodiment of FIGS. 1-6, and includes a strain block 205 to which is attached a strain gauge 210. The strain block 205 comprises a first grip lever, and a first pinch lever 205a is disposed at a first end of the first lever (strain block 205). A second lever 215 is attached to the strain block 205 remote from the first end of the first lever/strain block 205, and extends toward the first end of the first lever/strain block 205. A second pinch lever 215a is disposed at an end of the second lever 215 proximal the first end of the first lever/strain block 205. The second lever 215 also has an adjustable grip portion to accommodate the size of a hand of the user, including a grip bar 220 and a pair of grip supports 225.

For the deadlift exercise, a deadlift bar 230 is removably attachable to grip supports 225. A strap (not shown) is attached to strain block 205 via a strap centering pin 205b. The other end of the strap is attached to a floor plate (not shown) in the same manner as the embodiment of FIGS. 1-6.

In use, the strain block 205 and strain gauge 210 flex when first lever/strain block 205 and second lever 215 are squeezed by the user, or when first and second pinch levers 205a, 215a are pinched together by the user, or when bar 230 is pulled upwards.

Although certain specific examples have been disclosed, it is noted that the present teachings may be embodied in other forms without departing from the spirit or essential characteristics thereof. The present examples described above are considered in all respects as illustrative and not restrictive. The patent scope is indicated by the appended claims, and all changes that come within the meaning and range of equivalency of the claims are therefore intended to be embraced therein.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A functional capacity evaluator comprising:
   a strain block;
   a strain gauge attached to the strain block;
   a first pair of grips attachable to the strain block, and when a user squeezes the first pair of grips together using a grip motion, the strain block and strain gauge are flexed for measuring a grip strength of the user;
   a second pair of grips attachable to the strain block, and when the user squeezes the second pair of grips together using a pinch motion, the strain block and strain gauge are flexed for measuring a pinch strength of the user; and
   a deadlift bar attachable to the strain block, and when the strain block is supported in a first direction and the user pulls on the deadlift bar in a second direction opposite the first direction using a deadlift motion, the strain block and strain gauge are flexed for measuring a deadlift strength of the user.

2. The functional capacity evaluator of claim 1, wherein the first pair of grips includes a first lever fixed to the strain block, and a second lever movably attached to the strain block.

3. The functional capacity evaluator of claim 2, wherein the second lever is adjustably attached to the strain block to accommodate the size of a hand of the user.

4. The functional capacity evaluator of claim 3, wherein the second lever is slidably attached to the strain block.

5. The functional capacity evaluator of claim 4, wherein the strain block includes a plunger for adjusting a position of the second lever on the strain block, the second lever includes plural holes, and each of the plural holes is configured to receive the plunger.

6. The functional capacity evaluator of claim 4, wherein the strain block includes plural holes, the second lever includes a plunger for adjusting a position of the second lever on the strain block, and each of the plural holes is configured to receive the plunger.

7. The functional capacity evaluator of claim 2, wherein the second pair of grips includes a first pinch lever and a second pinch lever, and the first and second pinch levers are disposed at respective ends of the first and second levers of the first pair of grips.

8. The functional capacity evaluator of claim 1, wherein the deadlift measurement portion includes a bar with two grips.

9. The functional capacity evaluator of claim 8, wherein the deadlift bar includes a clamp portion for attaching the bar to the strain block.

10. The functional capacity evaluator of claim 9, wherein the bar and the clamp portion is detachable from the strain block.

11. The functional capacity evaluator of claim 9, wherein the strain block includes an attachment portion for attaching an anchoring member to the strain block for supporting the strain block in the first direction.

12. The functional capacity evaluator of claim 1, wherein the strain gauge is a single strain gauge.

13. The functional capacity evaluator of claim 11, wherein the anchoring member is a strap, and the attachment portion comprises a clevis for attaching the strap to the strain block.

14. The functional capacity evaluator of claim 1, wherein the first pair of grips includes a first lever and a second lever; and the second pair of grips includes a first pinch lever and a second pinch lever;
- wherein the first lever comprises the strain block, and the first pinch lever is disposed at a first end of the first lever;
- wherein the second lever is attached to the strain block remote from the first end of the first lever and extends toward the first end of the first lever, and the second pinch lever is disposed at an end of the second lever proximal the first end of the first lever; and
- the second lever comprises an adjustable grip portion to accommodate the size of a hand of the user.

* * * * *

UNITED STATES PATENT AND TRADEMARK OFFICE
CERTIFICATE OF CORRECTION

| | | |
|---|---|---|
| PATENT NO. | : 8,752,427 B2 | Page 1 of 1 |
| APPLICATION NO. | : 13/289614 | |
| DATED | : June 17, 2014 | |
| INVENTOR(S) | : Cyphery et al. | |

It is certified that error appears in the above-identified patent and that said Letters Patent is hereby corrected as shown below:

On the title page

(75) Inventors:

"Charles D. Cyphery, Albuquerque (MX); Marco N. Vitiello, Miami, FL (US)" should read --Charles D. Cyphery, Albuquerque, NM (US); Marco N. Vitiello, Miami, FL (US)".--.

Signed and Sealed this
Sixth Day of January, 2015

Michelle K. Lee
*Deputy Director of the United States Patent and Trademark Office*